United States Patent [19]

Koketsu et al.

[11] Patent Number: 5,233,033
[45] Date of Patent: Aug. 3, 1993

[54] METHOD FOR PRODUCTION OF SIALIC ACID

[75] Inventors: Mamoru Koketsu, Gifu, Japan; Hiroshi Kawanami, Yokkaichi; Lekh Raj Juneja; Masaru Fujiki; Hajime Hatta; Katsuya Nishimoto; Mujo Kim; Nagataka Yamazaki, all of Yokkaichi, Japan

[73] Assignee: Taiyo Kagaku Co., Ltd., Mie, Japan

[21] Appl. No.: 748,560

[22] Filed: Aug. 22, 1991

[30] Foreign Application Priority Data

Sep. 4, 1990 [JP] Japan .................................. 2-235434
Jul. 5, 1991 [JP] Japan .................................. 3-192427

[51] Int. Cl.$^5$ .............................................. C07H 1/00
[52] U.S. Cl. ...................................... 536/124; 536/127; 435/101; 435/105; 435/268; 435/274
[58] Field of Search ............... 435/101, 105, 268, 274; 536/124, 127

[56] References Cited

U.S. PATENT DOCUMENTS 4,888,324  12/1989  Catsimpoolas et al. ............... 514/25

OTHER PUBLICATIONS

Itoh et al., *Japanese J. Zootech. Sci.*, vol. 6(3); 277–282, 1990.
Juneja et al., *Carbohydrate Research*, vol. 214, pp. 179–186, 1991.
Kawanami et al., *Abstract XV Int'l Carbohydrate Symp.*, Yokohama Aug. 12–17, 1990.
Juneja et al., *Abstract XIII Jap. Carb. Symp.*, Osaka Jul. 31–Aug. 2, 1991.
Dialog Engl. Abstract of Jpn. Doc Laid-Open No. 69492.
Dialog Engl. Abstract of Jpn. Doc. Laid-Open No. 40491.
Dialog Engl. Abstract of Jpn. Doc. Laid-Open No. 34995.
Dialog Engl. Abstract of Jpn. Doc. Laid Open No. 16042.
J. Biol. Chem., 246 (2), 430–435; 1971.
J. Biol. Chem., 234 (8), 1971–1975, 1959.

*Primary Examiner*—Ronald W. Griffin
*Assistant Examiner*—Pamela S. Webber
*Attorney, Agent, or Firm*—Birch, Stewart, Kolasch & Stewart

[57] ABSTRACT

The present invention is directed to a method for producing crude sialic acid, comprising hydrolysis of a delipidated egg yolk and a method for producing high purity sialic acid, which comprises desalting a solution containing sialic acid obtainable by hydrolyzing a delipidated egg yolk, adsorbing sialic acid to an anion exchange resin and then eluting said sialic acid.

The present invention makes it possible to produce and purify sialic acid from delipidated egg yolk on an industrial scale.

8 Claims, No Drawings

METHOD FOR PRODUCTION OF SIALIC ACID

FIELD OF THE INVENTION

The present invention relates to a method of producing sialic acid in large amounts from delipidated egg yolk obtained as a residue in the production of polar lipids, neutral lipids, cholesterol and other substances from chicken egg yolk and a method of purifying crude sialic acid to high purity sialic acid on an industrially efficient scale.

BACKGROUND OF THE INVENTION

Sialic acid, a generic term for the acyl derivatives of neuraminic acid, occurs naturally in the form of a wide variety of derivatives, of which N-acetylneuraminic acid (Neu5Ac) is the most common.

In recent years, sialic acid has been found to act as a virus receptor and mediate various physiological actions such as cell recognition, cholera toxin neutralization, suppression of infection with pathogenic *Escherichia coli*, expectorant action and control of the hematologic half-life of blood proteins. With the increasing attention to sialic acid along with understanding of its biological roles, there have been increasing demands for its application to pharmaceuticals; for example, its supply in large amounts is strongly desired.

Although sialic acid occurs widely naturally in the non-reduced terminals of glycoproteins and glycolipids in vivo, it is difficult to produce sialic acid from a natural substance containing it both in a large amount and at a low cost and to purify it both on an industrial scale and to a high purity.

Reported methods for production of sialic acid include the method disclosed in Japanese Patent Laid-Open No. 34995/1989, in which sialic acid is produced from chick meconium, and the method disclosed in Japanese Patent Examined Publication No. 16042/1968, in which sialic acid is produced from chalaza and ovomucin obtained from chicken egg white, but none of these methods permits production of sialic acid both on an industrially large scale and at a low cost, since there is no system for industrial supply of the starting materials.

On the other hand, it is a known fact that sialic acid is present in egg yolk. However, egg yolk is used as nothing other than a raw material for mayonnaise, cakes and other foods. Industrial utilization of its components is limited to the use of egg yolk lipid as materials for cosmetics, pharmaceuticals and some foods; no one has ever attempted to industrially separate sialic acid from egg yolk.

This is because egg yolk has drawbacks in that the production process for sialic acid becomes troublesome and the cost is not favorable, since a large amount of lipid contained in egg yolk strongly emulsifies the egg yolk solution after hydrolysis in separating sialic acid from egg yolk, which in turn significantly hampers the purification process which follows.

As for a method for purification of sialic acid, Japanese Patent Laid-Open No. 34995/1989 discloses the method in which the starting material chick meconium is hydrolyzed and then adsorbed to anion exchange resin without being preceded by desalting, after which it is desalted. However, when this method is applied to production of sialic acid from delipidated egg yolk, it poses a problem, i.e., both the percent yield and purity of sialic acid are low so that high purity sialic acid cannot be industrially favorably obtained. Also, Japanese Patent Laid-Open No. 40491/1989 states that sialic acid can be purified by hydrolyzing a milk substance such as cow's milk, defatted milk, butter milk or whey, desalting the resulting hydrolyzate by electrodialysis and subsequently performing electrodialysis again. However, this method poses problems of decreased percent yield of sialic acid due to its loss during desalting and decreased purity of sialic acid due to the presence of salt impurities during purification as a result of the incapability of complete desalting.

SUMMARY OF THE INVENTION

It is an object of the present invention to develop and provide a method for production of sialic acid both in a large amount and at a low cost.

Accordingly, taking note of the circumstances described above, the present inventors made investigations of production of sialic acid. With the recognition that the extraction residue of egg yolk lipid, which is not efficiently utilized but which is used solely as livestock feed and mostly disposed as an industrial waste, is rich in sialic acid and suppliable both at a low cost and in a large amount, the inventors made further investigations and found that sialic acid can easily be obtained by hydrolyzing delipidated egg yolk and thus developed the invention.

Accordingly, the present invention relates to a method for production of sialic acid characterized by hydrolysis of delipidated egg yolk.

It is another object of the present invention to develop and provide a method of purifying the sialic acid thus obtained to high purity. Accordingly, the present invention also relates to a method of purifying sialic acid to high purity characterized in that the solution containing sialic acid obtained by hydrolyzing delipidated egg yolk is desalted, after which sialic acid is adsorbed to anion exchange resin and then eluted.

DETAILED DESCRIPTION OF THE INVENTION

The sialic acid for the present invention means a Neu5Ac or Neu5Ac-bound oligosaccharide among the neuraminic acid compounds. Although the Neu5Ac content is not subject to limitation, the above-mentioned sialic acids must each exist at least in the form of a free acid.

The delipidated egg yolk for the present invention means egg yolk obtained by delipidating raw egg yolk, dry powdered egg yolk, etc. by a conventional method using organic solvents such as methanol, ethanol or dimethyl ether. The maximum allowance for the residual lipid content in the total solid content is 20%, with preference given to egg yolk having a residual lipid content of not more than 10%. Contents exceeding 20% are undesirable, since emulsification occurs to hamper the purification process which follows.

To achieve hydrolysis, a process essential for making the sialic acid in delipidated egg yolk in a free form, both acid hydrolysis and enzyme hydrolysis are applicable with no limitation, but acid hydrolysis is preferred.

As for hydrolytic conditions in the case of acid hydrolysis, the delipidated egg yolk solution is adjusted to a pH of 0.6 to 2.5 by the addition of an acid such as sulfuric acid, hydrochloric acid or oxalic acid and then heated at 70° to 90° C., preferably 80° to 85° C. for 30 to 120 minutes, preferably 45 to 90 minutes, after which it is neutralized with a neutralizing agent such as barium hydroxide, sodium hydroxide or calcium hydroxide. The optimum pH for neutralization is normally in the range of from 5 to 6, under which conditions the amount of sialic acid adsorbed to anion exchange resin in the process which follows increases. If the pH is out of this range, incomplete liberation of sialic acid or decomposition of sialic acid will pose a problem.

In the case of enzyme hydrolysis, one or more enzymes such as neuraminidase, protease and sugar hydrolase are selected according to the purpose and deactivated by heating etc. after reaction under optimum conditions for respective enzymes.

Accordingly, neuraminidase yields Neu5Ac, while protease yields various Neu5Ac-bound oligosaccharides.

For example, enzyme hydrolysis is carried out normally at 20° to 60° C., preferably 35° to 45° C. in the presence of sialidase added to the starting material in a ratio of normally 100 to 3000 ppm, preferably 500 to 2000 ppm.

The hydrolyzate thus obtained is subjected to a known method such as filtration or centrifugation to remove the insoluble substances, after which it is concentrated under reduced pressure if necessary and dried by an ordinary method such as spray drying or lyophilization to yield crude sialic acid.

To obtain high purity sialic acid by purifying the crude sialic acid, the filtrate obtained by removing the insoluble substances from the hydrolyzate by a conventional method such as filtration or centrifugation is first subjected to a desalting treatment.

Any means of desalting can be used, as long as it is a traditionally known means, such as a reverse osmosis (RO) membrane filtration, electrodialysis or a dialytic membrane filtration. These means may be used singly or in combination. Particularly, the method using an RO membrane and/or electrodialysis is preferred. As an example of desalting using an RO membrane, the hydrolyzate is desalted through an RO membrane NTR-7250-S4F (produced by Nitto Denko Corporation) attached to a spiral type RO unit RSS-11X (produced by Nitto Denko Corporation). As an example of desalting by electrodialysis, the hydrolyzate is desalted through an electrodialytic membrane Neosepta CM-2 ACS (produced by Tokuyama Soda Co., Ltd.) attached to an electrodialytic apparatus TS-10-360 model (produced by Tokuyama Soda Co., Ltd.). As an example of desalting using a dialytic membrane, the hydrolyzate is placed in an 8/32 inch cellophane tube (produced by Wako Pure Chemical Industries, Ltd.), and after sealing the cellophane tube, the hydrolyzate is desalted with gentle stirring in a tank containing water in an amount about 10 times the amount of the hydrolyzate. Regardless of the desalting procedure, desalting is continued until the conductivity reaches normally 1500 μS/cm, preferably 900 μS/cm. Electrodialysis may be carried out in several stages; for example, the sialic acid and salts in the filtrate are allowed to pass an electrodialytic membrane in the first stage of electrodialysis, and the effluent is passed through a desalting membrane to allow nothing other than the salts to pass the membrane to yield a solution of sialic acid (desalted solution) in the second stage.

In the method of the present invention, the desalting procedure must precede the passage of the solution of sialic acid through anion exchange resin after hydrolysis. If the hydrolyzate is not desalted, the objects of the invention cannot be accomplished, since the amount of sialic acid adsorbed to anion exchange resin decreases considerably, and since the percent yield and purity of sialic acid decrease. This was found to be attributable to the influence of salts present in large amounts in delipidated egg yolk.

Next, the sialic acid in the desalted hydrolyzate is separated and purified using an adsorbent. In this process, anion exchange resin is used as a sialic acid adsorbent. In this case, an improving effect on the purity of sialic acid is obtained by using cation exchange resin in combination with anion exchange resin as necessary. Specifically, the desalted hydrolyzate is previously passed through cation exchange resin as necessary to adsorb the impurities such as amino acids thereto and further passed through anion exchange resin to adsorb sialic acid thereto. Examples of the cation exchange resin used for this purpose include Dowex 50W×2 (produced by Dow Chemical Company, USA), Amberlite IR-116 (produced by Japan Organo Co., Ltd.) and Diaion SK-102 (produced by Mitsubishi Chemical Industries, Ltd.). Examples of the anion exchange resin include Dowex 1×8 (produced by Dow Chemical Company, USA), Amberlite IRA401 (produced by Japan Organo Co., Ltd.) and Diaion SA11A (produced by Mitsubishi Chemical Industries, Ltd.).

The sialic acid adsorbed to anion exchange resin is recovered after elution with an organic or inorganic acid such as formic acid or hydrochloric acid or with a salt such as sodium chloride.

This eluate of sialic acid, after being desalted by a conventional method such as gel filtration or electrodialysis if necessary, is subjected to concentration under reduced pressure, membrane drying, spray drying or lyophilization to yield high purity sialic acid. The high purity sialic acid thus obtained can be used as a starting material for reagents and pharmaceuticals and for other purposes.

As stated above, the present invention makes it possible to produce and supply sialic acid both in a large amount and at a low cost, which has conventionally been difficult to realize. Furthermore, the invention will significantly contribute to the industry, if it is combined with production of egg yolk oil, whereby egg yolk is more efficiently utilized.

The present invention also makes it possible to purify sialic acid from delipidated egg yolk on an industrial scale, which has conventionally been difficult due to the influence of salts present in large amounts in delipidated egg yolk. In other words, the present invention permits the obtainment of sialic acid with almost 100% yield and purity by desalting the hydrolyzate before passing it through anion exchange resin.

EXAMPLES

Test Example 1

Preparation of delipidated egg yolk samples, quantitative determination of lipids and emulsification test 100 g of powdered egg yolk was delipidated by heating to 50° C. in an egg-plant shaped flask equipped with a condenser under the conditions shown below. Note that the delipidating temperature was 32° C. in the case of diethyl ether alone.

The results are shown in Table 1.

TABLE 1

| Lipid extraction from egg yolk | | |
|---|---|---|
| Extraction solvent | Extracted amount | Extraction Times |
| A. acetone following methanol | 1 l respectively | once |
| B. acetone following methanol | 1 l respectively | twice |
| C. acetone following methanol | 1 l respectively | three times |
| D. diethyl ether | 1 l | once |
| E. diethyl ether | 1 l | twice |
| F. diethyl ether | 1 l | three times |
| G. methanol | 1 l | once |
| H. methanol | 1 l | twice |
| I. methanol | 1 l | three times |
| J. acetone | 1 l | once |
| K. acetone | 1 l | twice |
| L. acetone | 1 l | three times |

50 g of each of the delipidated egg yolk samples A through L shown in Table 1 and a non-delipidated egg yolk sample was twice extracted with 500 ml of acetone at room temperature and then twice extracted with 500 ml of a 2:1 mixture of chloroform and methanol at 50° C. using a condenser, and the extracted lipids were quantitatively determined. Then, 10 g of each of the delipidated egg yolk samples A through L and a non-delipidated egg yolk sample was stirred using a homo-mixer in the presence of 30 ml of 0.1N sulfuric acid, after which the mixture was hydrolyzed at 80° C. for 1 hour, adjusted to a pH of 5.0 with a saturated solution of barium hydroxide and filtered. The filtrate was examined for the condition of emulsification. The lipids quantitatively determined were acetone-soluble lipids (%) and lipids soluble in the chloroform-methanol mixture (%). The condition of emulsification was evaluated in three grades: the filtrate is transparent and not emulsified (◯), the filtrate is slightly turbid (Δ), and the entire filtrate is completely emulsified (x).

The results are shown in Table 2.

TABLE 2

| Effect of lipid concentration of egg yolk powder on emulsification | | | | |
|---|---|---|---|---|
| | Lipids soluble in acetone (%) | Lipids soluble in CHCl$_3$ + CH$_3$OH mixture (%) | Total (%) | Extent of emulsification |
| Delipidated egg yolk sample | | | | |
| A. | 8.3 | 14.1 | 22.4 | Δ |
| B. | 3.5 | 12.5 | 16.0 | ◯ |
| C. | 2.3 | 9.8 | 12.1 | ◯ |
| D. | 20.8 | 14.8 | 35.6 | x |
| E. | 12.3 | 8.4 | 20.7 | Δ |
| F. | 9.8 | 7.1 | 16.9 | ◯ |
| G. | 35.2 | 5.1 | 40.3 | x |
| H. | 26.1 | 2.3 | 28.4 | x |
| I. | 21.8 | 0.2 | 22.7 | Δ |
| J. | 9.5 | 19.1 | 28.6 | x |
| K. | 5.6 | 17.5 | 23.1 | x |
| L. | 3.4 | 16.3 | 19.7 | ◯ |
| Non-delipidated egg yolk sample | 42.7 | 20.1 | 62.8 | x |

From the test results shown in Table 2, it is evident that emulsification does not occur so that the purification process which follows is not hampered when the total lipid content including the neutral lipids and phospholipids is not more than 20%.

Example 1

40 kg of the delipidated egg yolk sample B of Test Example 1 was suspended in 300 l of water. After adding 6N sulfuric acid to reach a pH of 1.4, acid hydrolysis was carried out with gentle stirring at 80° C. for 60 minutes. After completion of the hydrolysis, a saturated solution of barium hydroxide was added to reach a pH of 5.0. After filtering this mixture through a filter under pressure to remove the insoluble substances, the filtrate was concentrated under reduced pressure to yield 2.7 kg of crude sialic acid with a percent yield of 6.75%, relative to 40 kg of the delipidated egg yolk sample B. The percent yield relative to the theoretical amount of sialic acid contained in 40 kg of the delipidated egg yolk sample B was calculated to be 93% [calculated on the assumption that the theoretical percent content of sialic acid in delipidated egg yolk is 0.2% (Agricultural and Biological Chemistry, 46 (10), 2587–2589, 1982); the same applies below]. The Neu5Ac content was determined to be 2.8% as of purity by the resorcinol method. Here, the resorcinol method is based on "The Sialic Acid", 'XI. A Periodate-Resorcinol Method for the Quantitative Estimation of Free Sialic Acids and Their Glycosides', described in the Journal of Biological Chemistry, 246 (2), 430–435, 1971.

Example 2

40 kg of the delipidated egg yolk sample C of Test Example 1 was suspended in 300 l of water. After reaction with 1.0 kg of protease [Protease from Papaya (Type III), produced by Sigma] at a pH of 7.3 and a temperature of 37° C. for 12 hours, the reaction mixture was heated at 90° C. for 10 minutes to inactivate the enzyme. The resulting hydrolyzate was subjected to continuous centrifugation, and the precipitate was removed. The supernatant thus obtained was spray dried to yield 4.7 kg of crude sialic acid (Neu5Ac-bound oligosaccharide) with a percent yield of 11.7%, relative to 40 kg of the delipidated egg yolk sample C. The percent yield relative to the theoretical amount of sialic acid contained in 40 kg of the delipidated egg yolk sample C was 91%. To liberate Neu5Ac from this sialic acid product, hydrolysis was carried out, after which the Neu5Ac content was determined to be 1.5% as of purity by the resorcinol method.

Test Example 2

Percent yield and purity tests for sialic acid

Desalted and non-desalted delipidated egg yolk samples were prepared after hydrolysis. The sialic acid contained in each sample was adsorbed to anion exchange resin, and the percent yield and purity of sialic acid were compared among the samples on the assumption that the sialic acid content before column charging was 100%. Specifically, 30 l of water was added to 10 kg of each delipidated egg yolk sample. After hydrolysis with 6N sulfuric acid at a pH of 1.6 and a temperature of 80° C. for 1 hour, the hydrolyzate was neutralized to a pH of 6.0 with 6N barium hydroxide and filtered to yield 28 l of filtrate.

Then, the filtrate was subjected to the following three methods to determine the percent yield and purity of sialic acid.

1) 5 l of the filtrate was desalted using TS-10-360 (produced by Tokuyama Soda Co., Ltd.) until the conductivity reached 750 μS/cm, after which it was passed through Dowex 1×8 (1 l, formate type, produced by Dow Chemical Company, USA) to adsorb sialic acid. After water washing to remove the impurities, the sialic acid was eluted with formic acid, and the percent yield and purity were determined.

2) The percent yield and purity of sialic acid were determined using Dowex 1×8 in the same manner as in 1) above except that desalting was not performed.

3) The fraction eluted from Dowex 1×8 as directed in 2) above was desalted using TS-10-360.

As is evident from Table 3, when desalting does not precede the passage of filtrate through resin, the amount of sialic acid adsorbed to the resin decreases considerably and the percent yield of sialic acid is only less than 30%. In addition, the purity is as low as 50%. These figures demonstrate that the influence of salts is very great when delipidated egg yolk is used as a starting material.

On the other hand, when hydrolysis is followed by desalting until the conductivity reaches 750 μS/cm using an electrodialytic apparatus such as TS-2-10 (produced by Tokuyama Soda Co., Ltd.), sialic acid can be obtained with a percent recovery of almost 100% and a purity of almost 100% as determined by the TBA method. Here, the TBA method is based on "The Thiobarbituric Acid of Sialic Acids", described in the "Journal of Biological Chemistry", vol. 234, pp. 1971-1975.

These results demonstrate that desalting must precede the passage of filtrate through the column.

Example 3

400 kg of delipidated egg yolk was suspended in 1200 l of water. This suspension was adjusted to a pH of 1.6 by the addition of 6N sulfuric acid and subjected to acid hydrolysis with gentle stirring at 80° C. for 60 minutes. After completion of the hydrolysis, a saturated solution of barium hydroxide was added to reach a pH of 5.5. This mixture was filtered through a filter under pressure to remove the insoluble substances and then desalted. After completion of the hydrolysis, 1200 l of the hydrolyzate was desalted and concentrated to 50 l using an RO membrane NTR-7250 (produced by Nitto Denko Corporation). The resulting concentrate was passed through a column packed with Dowex 50W×2 (produced by Dow Chemical Company, USA, H type, 50 l) and further passed through a column of Dowex 1×8 (produced by Dow Chemical Company, USA, formate type, 50 l) to adsorb sialic acid to the resin. Then, the non-adsorbed undesired substances were washed down with 600 l of water. Elution was conducted on a formic acid density gradient from 0 to 2N to elute sialic acid. The fraction containing sialic acid was collected and dried under reduced pressure. The resulting dry solid was dissolved in 1 l of water and lyophilized to yield 675 g of sialic acid with a percent yield of 84%, relative to the theoretical amount of sialic acid contained in 400 kg of delipidated egg yolk. The purity of sialic acid was determined to be not less than 97% by the TBA method.

TABLE 3

| | Percent yield and purity for sialic acid of desalted or non-desalted samples after hydrolysis | | | | |
|---|---|---|---|---|---|
| | Sialic acid before column charging | Sialic acid in passed solution | Sialic acid in washing solution after column charging | Percent yield of sialic acid | Purity of sialic acid |
| Desalting followed by column chromatography | 100% | 0% | 0% | 99.3% | 97.6% |
| Non-desalting followed by column chromatography | 100% | 38% | 32% | 29.0% | 50.8% |
| Column chromatography followed by desalting | 100% | 39% | 30% | 32.0% | 75.8% |

Example 4

400 kg of delipidated egg yolk was suspended in 1200 l of water. To this suspension, 6N hydrochloric acid was added, and acid hydrolysis was carried out in the same manner as in Example 1. After completion of the hydrolysis, 4N sodium hydroxide was added to reach a pH of 6.5. This mixture was filtered through a filter under pressure to remove the insoluble substances and then desalted. 1200 l of the hydrolyzate was desalted until the conductivity reached 500 μS/cm using an electrodialytic apparatus (produced by Tokuyama Soda Co., Ltd.), after which it was passed through a column packed with Diaion SK102 (produced by Mitsubishi Chemical Industries Ltd., H type, 50 l) and further passed through a column of Diaion SA11A (produced by Mitsubishi Chemical Industries Ltd., formate type, 50 l) to adsorb sialic acid to the resin. Then, the non-adsorbed undesired substances were washed down with 600 l of water. Elution was conducted on a sodium chloride density gradient from 0 to 1N to elute sialic acid. The fraction containing sialic acid was collected, desalted by electrodialysis and dried under reduced pressure. The resulting dry solid was dissolved in 1 l of water and lyophilized to yield 683 g of sialic acid with a percent yield of 85%, relative to the theoretical amount of sialic acid contained in 400 kg of delipidated egg yolk. The purity of sialic acid was determined to be not less than 97% by the TBA method.

What is claimed is:

1. A method for producing sialic acid, comprising the steps of: hydrolyzing a delipidated egg yolk with acid; desalting the hydrolyzate; and then purifying the desalted hydrolyzate by treatment with ion exchange resin.

2. A method according to claim 1, wherein the residual lipid content in the delipidated egg yolk is not more than 20%.

3. A method according to claim 1, wherein said acid is HCl.

4. A method according to claim 1, wherein said acid is $H_2SO_4$.

5. A method according to claim 1, wherein said desalting is achieved by using a reverse osmosis membrane.

6. A method according to claim 1, wherein said desalting is achieved by using electrodialysis.

7. A method according to claim 1, wherein said treatment with ion exchange resin is achieved by using an anion exchange resin.

8. A method according to claim 1, wherein said treatment with ion exchange resin is achieved by using a cation exchange resin and an anion exchange resin.

* * * * *